(12) United States Patent
Kahn et al.

(10) Patent No.: US 7,705,723 B2
(45) Date of Patent: Apr. 27, 2010

(54) METHOD AND APPARATUS TO PROVIDE OUTBREAK NOTIFICATIONS BASED ON HISTORICAL LOCATION DATA

(75) Inventors: Philippe Kahn, Aptos, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 11/686,908

(22) Filed: Mar. 15, 2007

(65) Prior Publication Data

US 2007/0229290 A1 Oct. 4, 2007

Related U.S. Application Data

(60) Provisional application No. 60/782,985, filed on Mar. 15, 2006.

(51) Int. Cl.
*G08B 19/00* (2006.01)
(52) U.S. Cl. ............. 340/521; 340/539.13; 340/539.11; 340/539.1

(58) Field of Classification Search ................. 340/521, 340/539.13, 539.1, 539.11
See application file for complete search history.

(56) References Cited

U.S. PATENT DOCUMENTS

| | | | |
|---|---|---|---|
| 6,028,514 A * | 2/2000 | Lemelson et al. ...... | 340/539.13 |
| 6,031,455 A | 2/2000 | Grube et al. | |
| 6,608,559 B1 * | 8/2003 | Lemelson et al. ...... | 340/539.13 |
| 2006/0036619 A1 | 2/2006 | Fuerst et al. | |

OTHER PUBLICATIONS

International Search Report and Written Opinion, PCT/US07/06644, Jul. 17, 2008, 8 pages.
Supplementary Search Report, EP07753284.4, Aug. 19, 2009, 5 pages.

* cited by examiner

*Primary Examiner*—Daryl Pope
(74) *Attorney, Agent, or Firm*—Blakely, Sokoloff, Taylor & Zafman, LLP; Judith A. Szepesi

(57) ABSTRACT

A method and apparatus to collect user location data over time, correlating user location data with outbreak data. The method and apparatus further comprising an alert mechanism to indicate to a user if there was a potential exposure.

20 Claims, 8 Drawing Sheets

Initial Data:

Format: DMM M/D/Y H:M:S -8.00 hrs Datum[104]: WGS 84
T 05/30/1999 14:46 47°11.839' -120°57.156'
T 05/30/1999 14:47 47°11.843' -120°57.192'
T 05/30/1999 14:48 47°11.845' -120°57.205'
T 05/30/1999 14:49 47°11.894' -120°57.363'
T 05/30/1999 14:50 47°12.001' -120°57.658'
...

Location Processed Data:

T 5/30/1999 14:46-15:20 Moving, location correlates to train (2 p.m. train to Denver, ~car 2
T 5/30/1999 15:20-15:30 Stationary, location correlates to I-25 & Broadway station
T 5/30/1999 15:30-15:40 Moving, location correlates to streets
T 5/30/1999 15:40-15:45 Moving, location correlates to home
T 5/30/1999 15:45-16:45 Stationary, location correlates to home
...

Pruned Data:
5/30/1999 Train to Denver, Broadway Station, home

Alternative Pruned Data:
5/30/1999 2 p.m. train to Denver, 3:20-3:30 Broadway station, 15:40-16:45 Home.

Alternative Usual-Process Comparison Data:
(Link to standard behavior #2)
5/30/1999 15:20-15:30 Broadway station Contact Processed Data:

T 5/30/1999 14:46-15:20 Proximity to Numbers X, Y, Z
T 5/30/1999 15:20-15:30 Proximity to Numbers A, B, C
T 5/30/1999 15:30-15:40 No proximate numbers
T 5/30/1999 15:40-15:45 No proximate numbers
T 5/30/1999 15:45-16:45 Proximity to number W

Fig. 6

Health Dashboard

Manage my:
  Pedometer
  Cardio Fitness
  Sleep
  Weight
  Blood Pressure
  Blood Glucose
  Cholesterol Messaging Health News Pandemics Reports Setup my:
  Contacts
  Alerts & Sharing
  Communications
  Health Monitors
  Information Your Overall Threat Level: MEDIUM Critical Messages: (Day 14 since first Human Influenza Outbreak in US)

➤ Morning Commute Clear from 777 Hudson Lane to 1200 Pacific Avenue
  No immediate local threats at this time.

⚠ ALERT: Confirmed Outbreak San Jose Airport      complete report
  34.4 miles away, 3:14 pm 3/14/06                view outbreak map
  You passed within 3.2 miles of this location 2 days ago Local Threat Map:

Confirmed Outbreak at San Jose Airport 34.4 miles away, 3:14 pm 3/14/06
➤ You Passed within 3.2 miles of this location 2 days ago.

Key Resources:

Confidential location watch enabled to protect your health.
    ● Enabled   ○ Disabled None of your locations in the past 14 days put you at risk.

Check the status of an address or route for ground transportation:
    ● Route    ○ Address
      from: [                    ] (address, city, state)
      to:   [                    ] (address, city, state)
                                              (enter)

Check the health safety of a flight reservation:
    airline: [▼]  flight number: [▼]  leaving: [    ]
                                              (enter)

What You Should Know:
Critical Facts   Infections in Humans    CDC      Vaccine Development
Current Situation   Past Outbreaks    World Health Org.   Infection Control
Tamiflu Information

Fig. 7

METHOD AND APPARATUS TO PROVIDE OUTBREAK NOTIFICATIONS BASED ON HISTORICAL LOCATION DATA

This application claims priority to Provisional Patent Application Ser. No. 60/782,985, filed Mar. 15, 2006.

FIELD OF THE INVENTION

The present invention relates to notifications, and more particularly to notifications of outbreaks.

BACKGROUND

Historically speaking tracking epidemic and pandemic outbreaks is extremely difficult, except after the fact. Especially for diseases which may have a longer incubation period, such as bird flu, determining the origin of an outbreak is difficult. Furthermore, alerting possibly infected individuals is difficult, if not impossible.

BRIEF DESCRIPTION OF THE DRAWINGS

The present invention is illustrated by way of example, and not by way of limitation, in the figures of the accompanying drawings and in which like reference numerals refer to similar elements and in which:

FIG. 6 is an exemplary data listing in various stages.

FIG. 7 is an exemplary screen shot of an outbreak report system which may be incorporated into a healthcare system.

DETAILED DESCRIPTION

Figure 1:
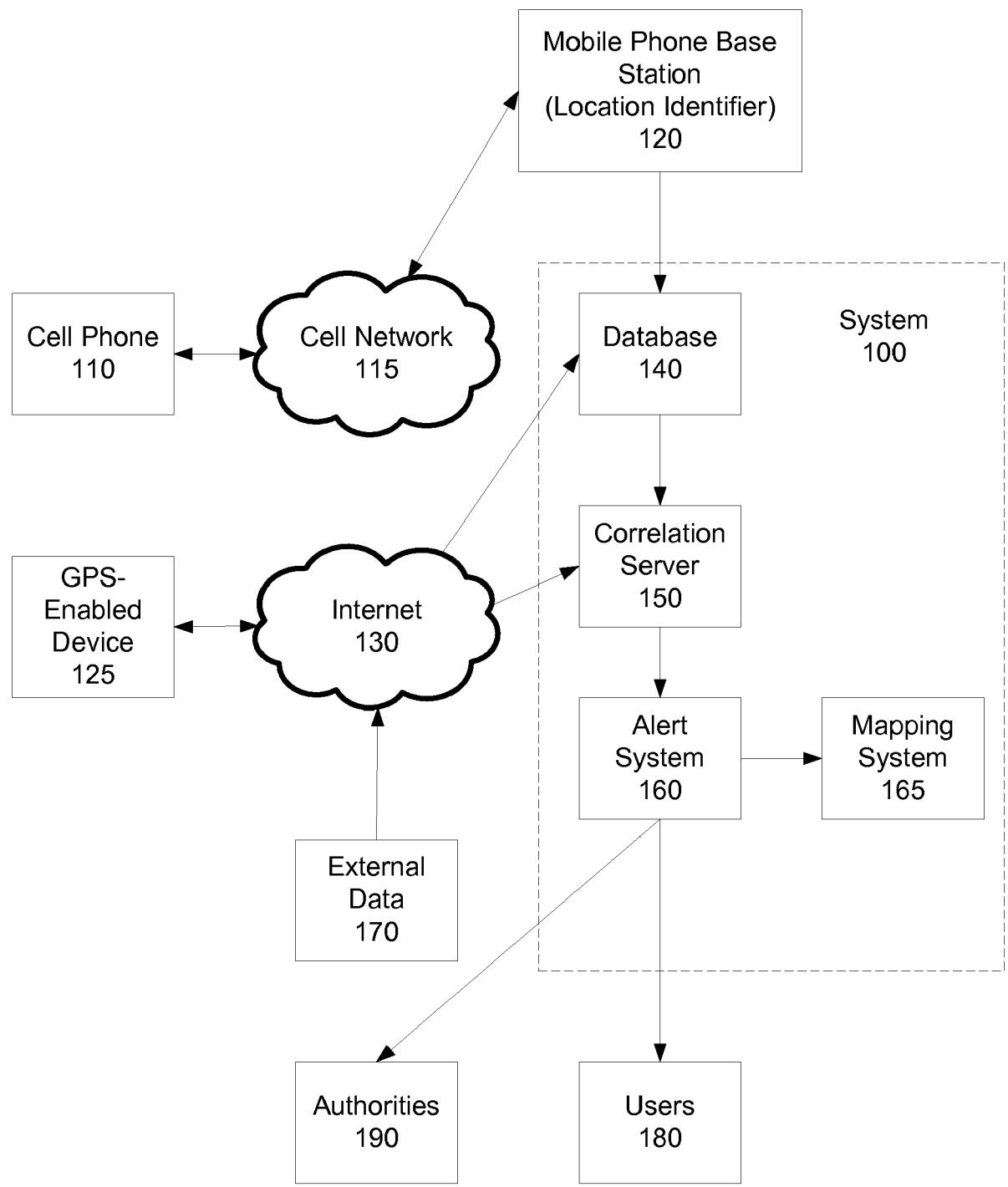
FIG. 1 is an exemplary network diagram of the system including the various elements which may be connected to it.

The method and apparatus described is a way to provide a handle on outbreaks of various diseases, pandemics, or health threats of various sorts. The system receives location information from users, user systems, or other systems. User systems may utilize global positioning system (GPS) data, or a cellular network to obtain location data. The system then utilizes a correlation server to look at proximity of various cell phones, user systems, or other devices to each other, and to any events of interest. In order to help determine this, in one embodiment the algorithm looks at location information combined with local maps and events. For example, location data may be mapped to actual locations such as movie theatres, restaurants, malls, public places. For example, people moving at the same relatively high speed along streets are probably in the same car etc. The system determines, for each location-enabled user, a list of the close encounters (with other location-enabled users). In one embodiment, this data is retained for a period of time. In one embodiment, this data is pruned over time. In one embodiment, the period of time is a function of the incubation times of various viruses, bacteria, etc. which may be of concern during the current period.

The system receives data that an individual or "point source of disease" has been identified either from the individual if he or she is a user, from a doctor, or from another source (such as news, Center for Disease Control (CDC), or other reporting entity.) The system at that point backtracks all contacts for the affected individual, as far as possible. In one embodiment, if the individual is a system user, the system has past location data available. In one embodiment, if the individual is not a system user, reporting data from the CDC and other sources may be used to identify a travel path of the individual. Note that while the term "user" and "individual" the disease source may be non-human. For example, a chicken transported to a farmer's market may be the originating disease vector. For the purposes of this patent, the chicken may be referred to as the "individual." Similarly, if the breakout is caused by a chemical spill or similar incident, the tracking data may utilize this "point source" as the "individual" that has become sick.

This backtracking, in one embodiment includes checking for corresponding/related illnesses. The system, in one embodiment, alerts anyone who has been in close contact with the affected point source, as well. In one embodiment, close contact may be defined differently for various outbreaks. For example, for something that involves airborne bacteria, close contact may be being in the same car, office, airplane, movie theatre, restaurant, enclosed space, etc. On the other hand for bacteria that propagates via physical contact, closer proximity may be used as the guide for alerting users.

In one embodiment, the system looks for possible sources of infection by backtracking and looking at these "logical trees" for each person in the close contact universe of the affected user. In one embodiment, the user's data, as well as backtracking data, may be provided to appropriate authorities. In one embodiment, the user controls this backtracking. That is, the system informs the user that he or she may have been affected, and the user determines whether tracking data should be analyzed. In one embodiment, the user controls informing the authorities as well. In one embodiment, data may be provided to authorities without identifying information, to protect the privacy of the user.

This data may be used for identifying areas which may be affected, paths of infection, quarantine, distributions of medicine, etc. The data may be useful to understand, manage, and potentially contain any outbreaks. In one embodiment, the system can present a map of the outbreak as well. In one embodiment, the map may describe the historical progression of the outbreak and may help in predicting its spread.

This is a system that finally can get a handle on the real-time understanding, management, and containment of outbreaks of disease, including potentially pandemics. By tracking historical location information, it can provide historical and currently relevant data. Until now not much could be done. But with ubiquitous cellular telephones and communications networks, the ability to constantly be aware of users' locations has been created. This tool may be vital in the future as trade and travel becomes more and more global, and treatment resistant diseases emerge.

FIG. 1 is an exemplary network diagram of the system including the various elements which may be connected to it. The system 100 includes a database 140, correlation server 150, alert system 160, and mapping system 165. In one embodiment, these elements of system 100 may be located on separate servers or devices. In another embodiment, the system 100 may be located on a centralized server system. In another embodiment, the named elements (i.e. database 140, correlation server 150, etc.) may each be a distributed system, distributed over multiple systems. In one embodiment, correlation server 150 may distribute its calculations across a wide network of devices. In one embodiment, the system 100 may be part of a SIMS system. The SIMS system is a sensor/monitor/device (SMD) Integration and Management Server (SIMS).

User location data is received via either user cell phones 110 or other GPS or location enabled devices 125. In one embodiment, for cell phones 110, the location data may be received from a mobile phone base station (location identifier) 120. The location data is added to database 140.

Correlation server 150, in one embodiment, adds location identification data (i.e. car, train, office, movie theater, etc.) In one embodiment, correlation server 150 also adds pointers to other users whose locations coincided with the user's location. In one embodiment, the co-location must be for a sufficiently long time or in a sufficiently enclosed area to trigger a proximity correlation. For example, passing in the street would not trigger a proximity correlation, but spending even 10 minutes in an enclosed subway car may.

The alert system 160 receives alerts from users, or from external data sources 170. In one embodiment, the alert system 160 obtains data from the SIMS server (shown in FIG. 2) which provides user health monitoring information. In one embodiment, the alert system 160 further interacts with external systems 170, such as the CDC, news providers, and other relevant data sources to monitor for outbreaks.

When an outbreak is identified, the alert system uses the correlated data from database 140, to send alerts to the appropriate users 180. In one embodiment, only those users who opt into the system receive alerts. In one embodiment, users have the privacy option of leaving their location out of the system. However, in that case they do not receive alerts, and are effectively excluded from this system. In one embodiment, the alert system 160 further notifies appropriate authorities of an outbreak. The appropriate authorities, in one embodiment, may include the Center for Disease Control (CDC), local healthcare workers, local pandemic/outbreak specialists, and others.

Mapping system 165 can provide mapping of the spread of an outbreak, based on data from users. In one embodiment, mapping system 165 provides current as well as historical maps. In one embodiment, mapping system enables a user to enter location & time data, to determine whether the user may have been impacted by an outbreak. In one embodiment, a user may request alerts of significant outbreaks, even if his or her own location does not coincide with the outbreak. The user may, in one embodiment, also browse outbreak maps. This enables users who opt out of the alert system to derive some benefit from the system.

In one embodiment, user locations are monitored through periodic data from user devices such as GPS data or cell phone data. In one embodiment, the system also calculates "projected data" for a user. For example, if a user is generally at work between 9 a.m. and 5 p.m. on weekdays, the system may assume this location, even if the user failed to take his or her cell phone or other location-enabled device. This may provide "projected contact" data, based on historical records of user behavior. In one embodiment, correlation logic 150 generates this data. In one embodiment, once a user pattern has been strongly established, the correlation database may simply store an indicator, showing that the pattern has been followed. This may reduce the amount of data stored in database 140.

Figure 2:
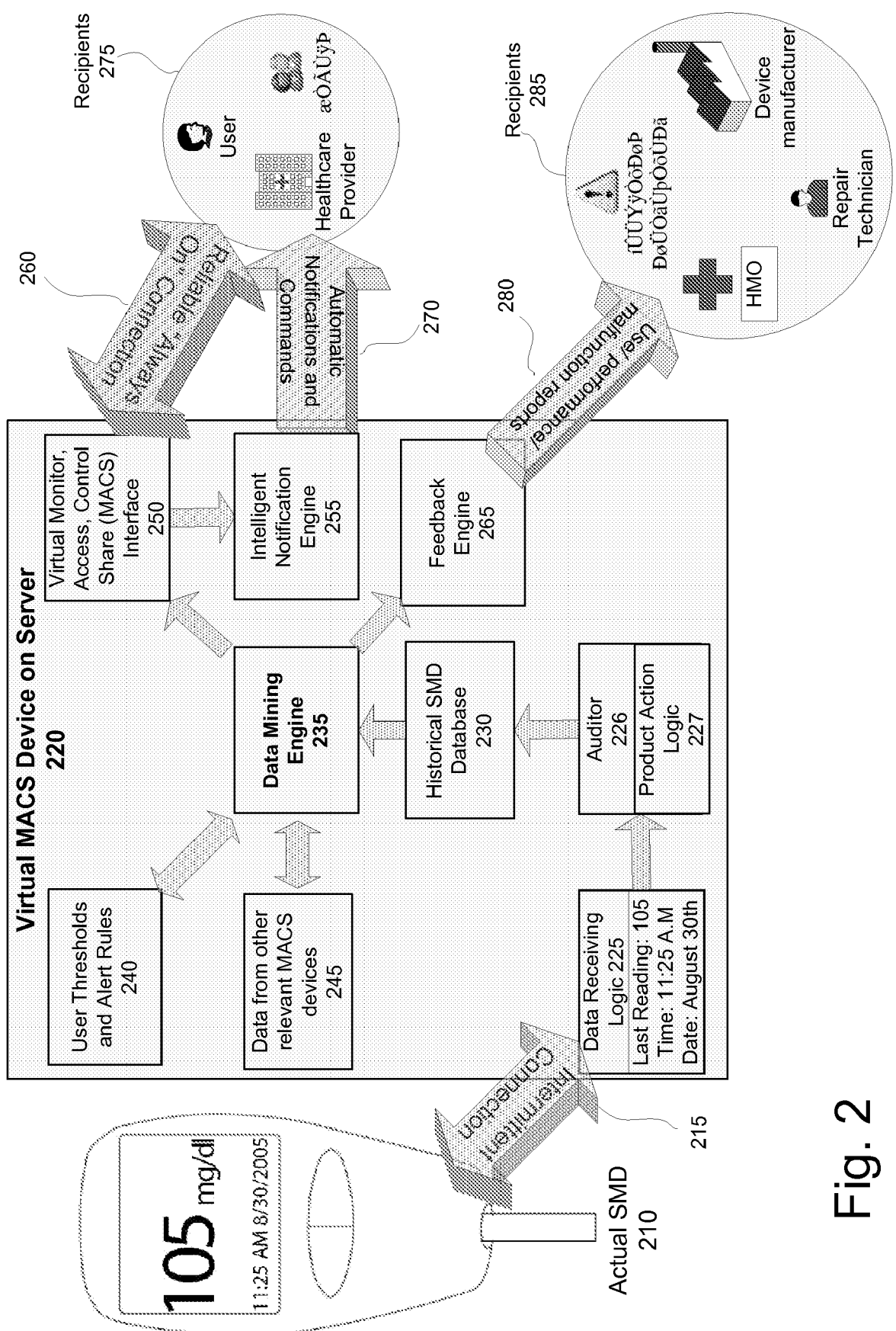
FIG. 2 is a block diagram of one embodiment of a server system which may be used with the present invention.

FIG. 2 is a block diagram illustrating one embodiment of the MACS device and its relationship to the actual SMD. The actual SMD 210 has an intermittent connection 215 to a server 220. The connection 215 may be through the Internet, through a carrier network, or through other means. The server 220 may be located in the same location as the real SMD 210.

The data receiving logic 225 receives the data from the actual SMD 210 via an intermittent connection 215. The data is stored in historical database 230. The historical data is used by data mining engine 235, to present virtual MACS device 255 via a reliable always-on connection 265 to various recipients 290. In a healthcare setting for example, the recipients may include the user, healthcare providers, and family. For environmental monitors, the recipients may include the responsible local and state officials, local residents, or other relevant recipients.

In one embodiment, data mining engine 235 may further interface with user alerts and rules 240 to generate notifications through intelligent notification engine 250. Intelligent notification engine 250 can send automatic notifications to designated recipients 290, when certain threshold or alert conditions are met. The threshold or alert conditions may include historical data, trend analysis, variance from charted trends, simple threshold, or any combination of the use of historical and current data from the actual SMD 210. In one embodiment, the data mining engine 235 constantly monitors the database 230, to ensure that the alert rules and user thresholds 240 have not been triggered. Intelligent notification engine 250 can, in one embodiment, trigger a notification in an appropriate format to any designated recipient.

In one embodiment, in addition to the database 230, data from other relevant actual SMDs may be received as well via logic 245. For example, in an environmental situation, in addition to the wind speed, the barometric pressure, or other relevant conditions may be monitored. The threshold and alert rules 240 may utilize a combination of data from more than one real SMD to trigger a notification or command 270.

Figure 8:
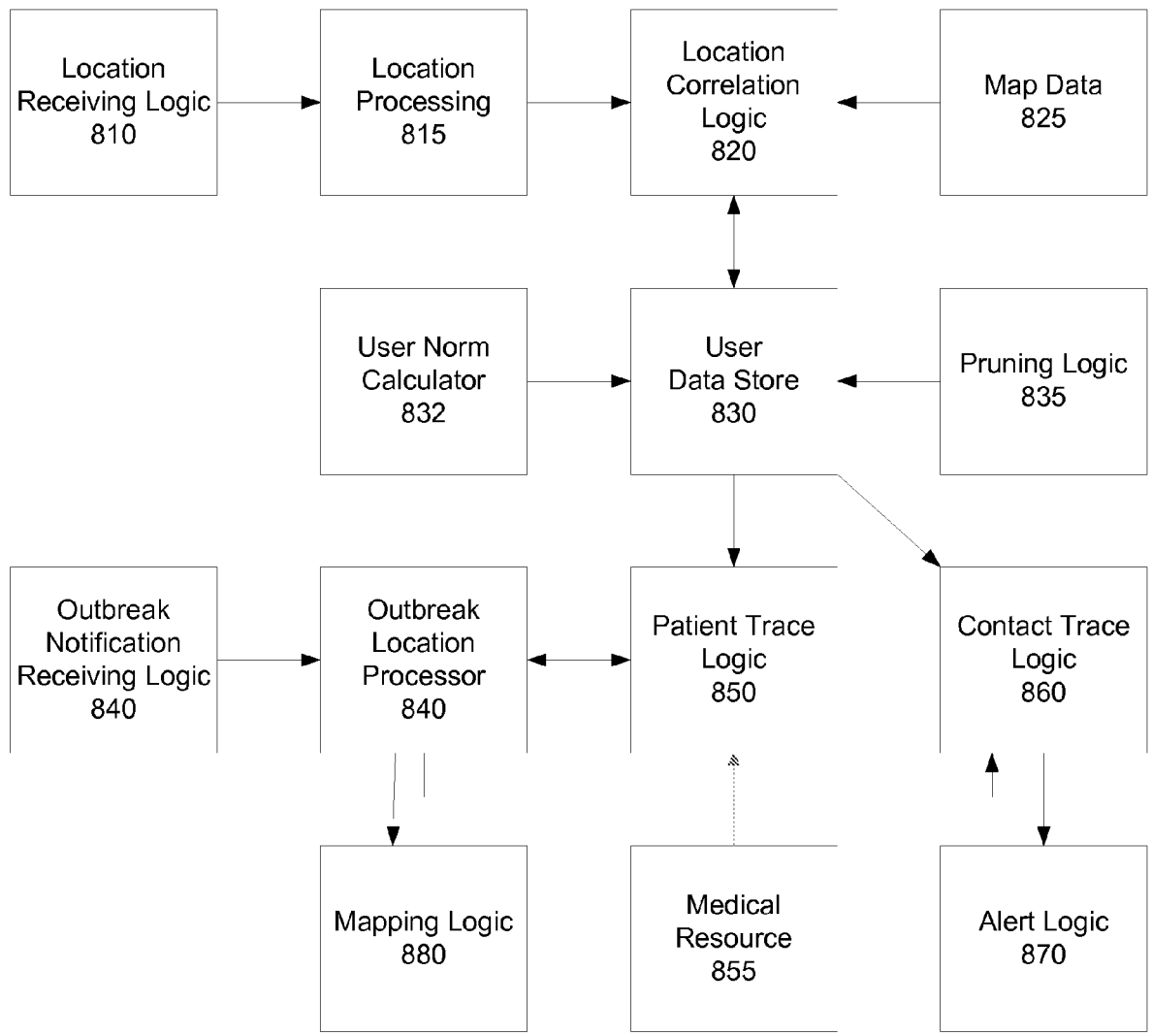
FIG. 8 is a block diagram of one embodiment of the outbreak notification system.

FIG. 8 is a block diagram of one embodiment of the outbreak notification system. The location receiving logic 810 receives location data from users. In one embodiment, location data may be in various formats, as dictated by the data source. For example, data from a GPS device appears different than data from cell towers. At block 815, the location processing logic translates the location data into a preferred format. In one embodiment, the format may be a longitude/latitude.

Location correlation logic 820 uses map data 825, to map the user's location(s) to actual map locations, i.e. train, train station, bus, office, home, etc. In one embodiment, data already in the user data store 830 may be utilized. In one embodiment, the user data store 830 stores the user's locations. In one embodiment, the user data store 830 also includes user normal behavior, as calculated by the user norm calculator 832. In one embodiment, a single user may have multiple "norm" sets. For example, the user may have a different normal behavior pattern for workdays and weekends.

Outbreak notification receiving logic 840 receives outbreak notifications from users. In one embodiment, outbreak notification receiving logic 840 may periodically poll external data sources such as CDC press releases, news, etc. to identify outbreaks.

Outbreak location processor 840 determines the location(s) associated with the outbreak notification. Patient trace logic 850 determines the locations of the infected person during the incubation period of the identified outbreak. In one embodiment, medical resource 855 is used to determine a length of incubation. The user data store 830 is used in this determination. The outbreak location processor 840 uses this data to construct a timeline of outbreak locations. Contact trace logic 860 then determines what other users, if any, where In sufficiently close contact to the patient that they may be at risk. Any such users are alerted by alert logic 870. In one embodiment, appropriate agencies and healthcare providers may also be notified.

In one embodiment, mapping logic 880 utilizes the patient trace and outbreak process to generate a progressive map, showing the spread of the outbreak as determined by the system.

Figure 3:
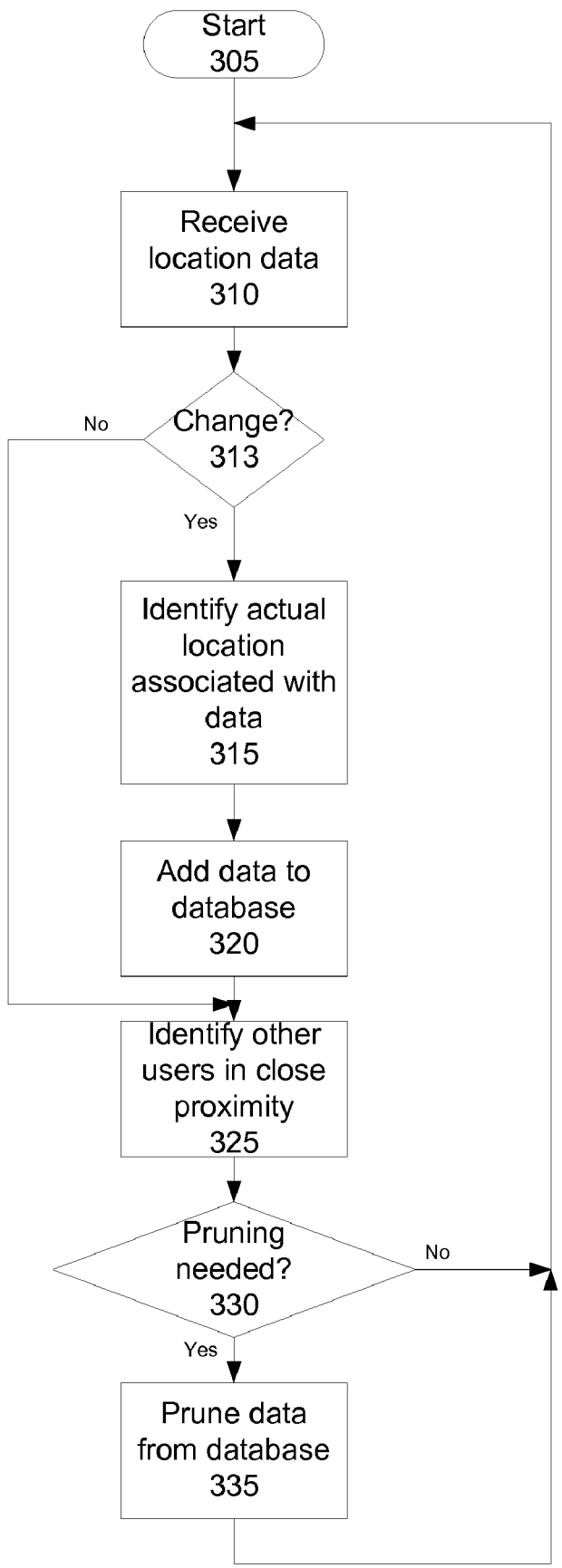
FIG. 3 is a flowchart of one embodiment of obtaining data and correlating data.

FIG. 3 is a flowchart of one embodiment of obtaining data and correlating data. The process, in one embodiment, is continuously running on the server. At block 310, location data is received from the user. The location data, in one embodiment, is sent automatically by the user's device. The user's device, as noted above may be a mobile phone, a mobile communicator of any sort, or a GPS enabled device of any sort. In one embodiment, if the user's device is a cellular telephone, in one embodiment whenever the cellular telephone checks in with the local cell towers, the location data is passed on to the server.

At block 313, the process determines whether the user's location has changed. If the user's location has not changed, the process continues to block 325. If the user's location has changed, the process continues to block 315.

At block 315, the actual location associated with the location data is identified. In one embodiment, the actual location may include places such as stores, sidewalks, office buildings, homes, subway cars, vehicles, etc. In one embodiment, prior location data is taken into consideration when identifying current location. For example, a user who appears to be traveling rapidly along locations which define train tracks or stations is likely to be on the train. Similarly, speedy travel along roadways generally signifies traveling in a car, bus, or motorcycle. In one embodiment, the user may be asked to identify mode of travel, if it cannot be determined.

At block 320, the user's location data is added to the user database. In one embodiment, the location data is not just a physical location (i.e. 123 Main Street) but rather a relative location (i.e. Starbucks Coffee Shop on 123 Main Street). This is more useful data, since being in close proximity to others is a determining factor in the spread of many illnesses.

At block 325, other users in close proximity are identified. In one embodiment, this may alter the location. For example, if it appears that the user is traveling at the same speed/direction as a group of others, he or she is more likely to be on a bus, rather than on a motorcycle. In one embodiment, indicators of other users' locations are added to the database. In another embodiment, the correlation is only calculated when an outbreak or illness is identified.

At block 330, the process determines whether it is time to prune the user's database. Pruning, in one embodiment, reduces the amount of data being stored about the user's past movements. In one embodiment, pruning is triggered by a timer, i.e. if there is data that is older than a certain time, it is pruned. If no pruning is needed, the process returns to block 310, to continue collecting data.

If it is time for pruning the process continues to block 335. In one embodiment, the oldest data is pruned. In another embodiment, data that is likely not to lead to exposure is pruned first. For example, data about situations in which the user was either in a large public area (i.e. a park) or alone in an enclosed space (i.e. car, motorcycle, home, etc.) is pruned by preference. In one embodiment, higher risk locations, such as airports, malls, etc. are retained longer than lower risk locations. In one embodiment, the system rates each location by risk factor, data collection level (i.e. number of users in area), and time (i.e. time since data was collected). The location having the lowest overall score is trimmed. The lowest overall score is generally data that is old, from an area with few other users, and from an area with an overall low risk factor. The user's database is pruned, in accordance with the preset rules, at block 335. The process then continues to block 310, to continue collecting data.

In this way, the system continuously accumulates location data about a user, and makes this data available. The below figures discuss in more detail how this data is used.

Figure 4:
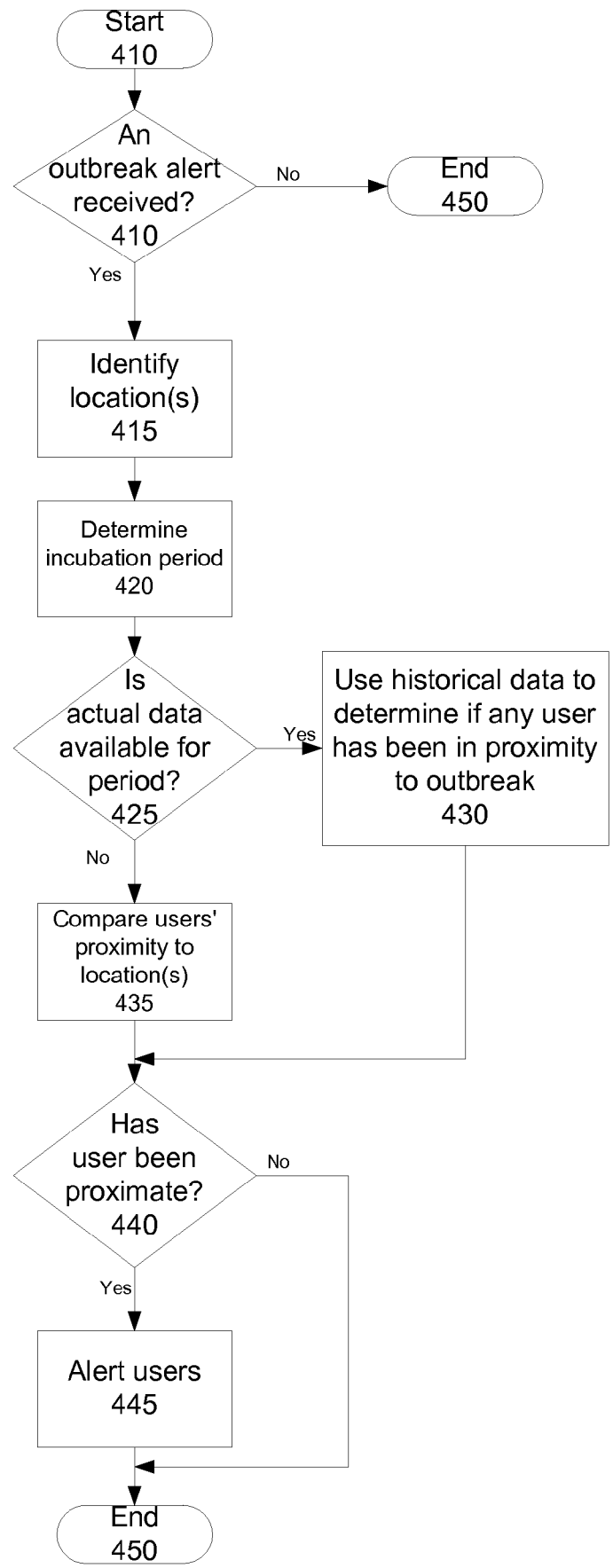
FIG. 4 is a flowchart of one embodiment of what happens when an alert is received.

FIG. 4 is a flowchart of one embodiment of what happens when an alert is received. Outbreak alerts may be received from users, news, or other sources. At block 410, the process determines whether an outbreak alert has been received. If not, the process ends. Note that while this is shown in flowchart form, as are other portions of these processes, these processes may actually be interrupt driven, such that the process only starts when an outbreak alert is received. In one embodiment, the system periodically polls available news sources to identify any outbreaks which may warrant an outbreak alert.

At block 415, the location(s) of the outbreak alert are identified. In one embodiment, depending on the type of outbreak alert received, this may be a complex process. For example, if the outbreak alert is received from a user, the user's own data from the system may be utilized to determine locations. If the outbreak alert is received from the CDC, the outbreak alert may be more broad, indicating a zone in which the outbreak was centered.

At block 420, the incubation period for the identified outbreak is determined. Various diseases have longer or shorter incubation periods. For example, the Hanta Virus Hantavirus has an incubation period of 2-4 weeks in humans, before symptoms of infection occur. Thus, when a user reports symptoms, the system calculates back to identify period(s) during which the diseases was infectious, even if symptoms were not yet showing.

At block 425, the process determines whether there is actual data available for the period of incubation. For example, if the outbreak if received from a user, indicating that the user has been infected, then there is actual location information for that user during the incubation period. However, if the data is received from a news report indicating that certain individuals fell ill with a disease, there may not be data about the location of those individuals during the incubation/infectious period.

If actual data is available, then at block 430 historical data of user locations are used to determine if any user has been in proximity to the outbreak path during the incubation period. If not, at block 435 users' proximity to the known outbreak location(s) is calculated.

At block 440, the process determines whether any user has been proximate. If so, the affected users are alerted, at block 445. In one embodiment, appropriate third parties may also be alerted. These third parties may include the healthcare providers for the affected users, disease control agencies, etc. If there are no affected users, the process ends at block 450.

Figure 5:
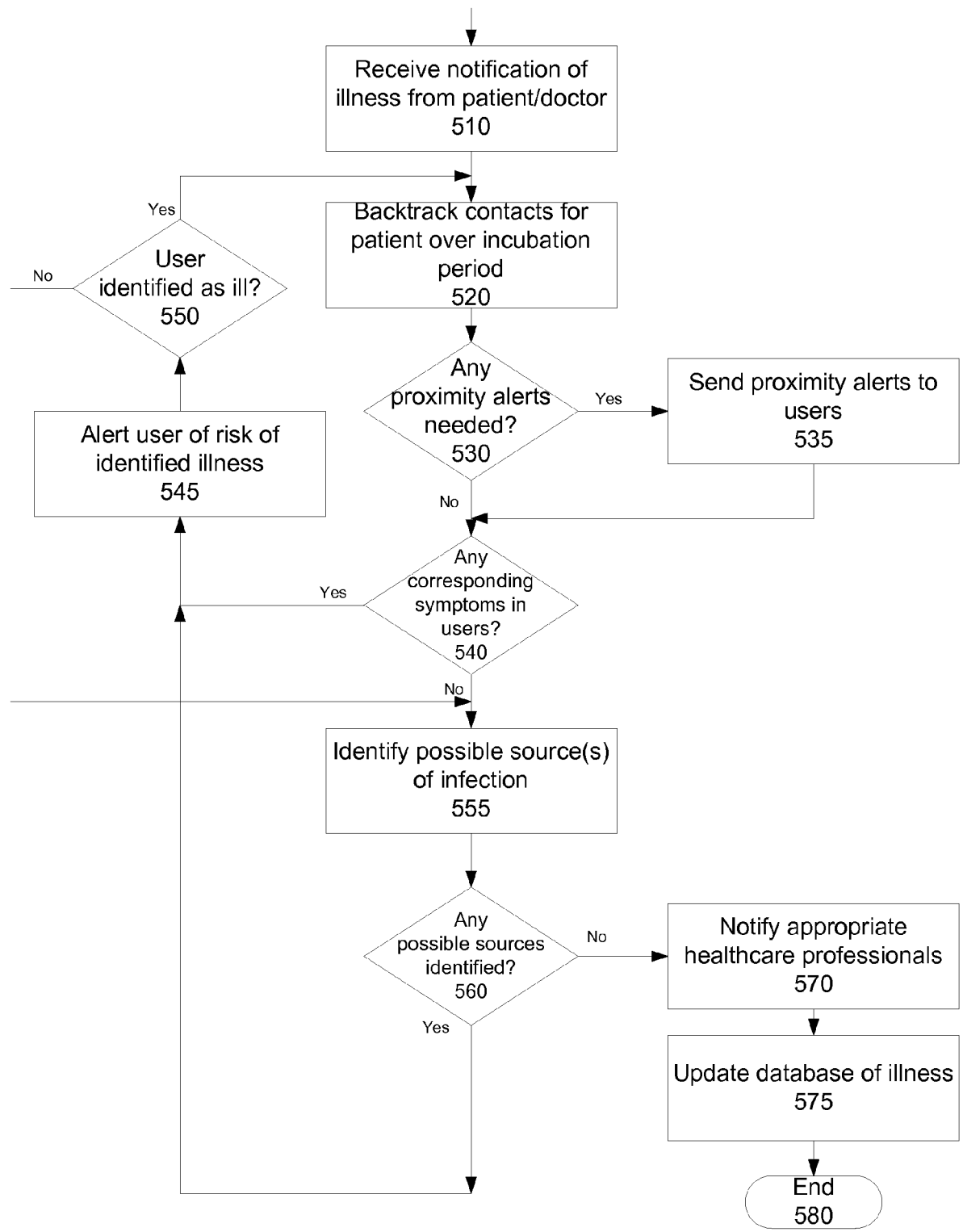
FIG. 5 is a more detailed flowchart of one embodiment of how outbreak alerts are handled.

FIG. 5 is a more detailed flowchart of one embodiment of how outbreak alerts are handled. At block 510, a notification of an illness or outbreak is received from a patient, doctor, or third party.

At block 520, the contacts for the patient are backtracked, over the incubation period. In one embodiment, the longest period likely to be the incubation period are backtracked to.

At block 530, the process determines whether there are any proximity alerts needed. Proximity alerts are needed when there are one or more other users who were in proximity to the patient during the incubation period. If proximity alerts are needed, then at block 535 the appropriate alerts are sent to the user, their designated contacts, and any appropriate agencies.

At block 540, the process determines based on the health data in the MACS system, whether there are any detected corresponding symptoms. For example, if the outbreak is Hantavirus, the process determines whether any possibly affected users have shown the symptoms associated with the virus, during any of its stages. In one embodiment, this determination is restricted by geographic location of the originally identified infection/source.

If corresponding symptoms are identified, the process continues to block 545. At block 545, the process alerts the user, and appropriate authorities that the user may have the illness. At block 550, the process determines whether there has been confirmation that the user has the illness. If so, the process continues to block 520, to backtrack contacts for this newly identified patient.

Otherwise, the process continues to block 555. At block 555, the process attempts to identify possible sources of infection, for the initial patient, or any other identified patients. In one embodiment, symptom matching is used. The process determines if any possible sources have been identified, at block 560. If a source is identified, the process continues to block 545, to notify the potential source. If no sources are identified, the appropriate health authorities are notified at block 570. At block 575, the database of the illness is updated with the additional information, and the process ends at block 580.

In this way, a single report of illness may result in multiple potentially exposed patients being warned, and informed of the risk. Furthermore, since each positively identified patient is then followed-up with a similar process, in one embodiment, the spread of the disease may be traced. Note that while the term "illness" is used any type of infectious exposure may be considered an illness for the purposes of this analysis. Further note that this may be an interrupt driven process, as could other processes shown as flowcharts in the present application. The use of the flowchart format is simply to show one possible sequence of events. However, the flowcharts are not meant to limit the activities in the sequential order shown in the flowchart.

FIG. 6 is an exemplary data listing in various stages. In one embodiment, data is initially provided as simple GPS latitude/longitude data.

The data is then processed to indicate actual locations. Note that the location-processed data is significantly more compact and informative than the original data set.

Pruned data in one embodiment simply shows the locations which the user has visited during the day. Alternative pruned data shows times and locations for high risk environments, while low risk environments are not included.

In one embodiment, the data is compared to a "standard" processed data, which is the user's normal behavior, and only changes from the normal behavior are noted. Thus, in this instance, if the user always takes the 2 p.m. train, the only logged information is that the user spent 10 minutes at Broadway station. In one embodiment, this indicates that this is a change from the user's normal behavior. The user's normal behavior may be to spend more or less time at the station.

In one embodiment, the data may be contact processed, to identify which other individuals the user has come in contact with. In one embodiment, this processing is only performed when an illness/problem is identified. In one embodiment, the default storage format for new data is as location processed data or usual-comparison data. In one embodiment, as data ages it is pruned. In one embodiment, an initial pruning removes low risk data (i.e. home, in car, etc.). The data then may be further pruned as it ages further. Finally, in one embodiment after the incubation period of the infections that are being considered have passed, the data is deleted.

FIG. 7 is an exemplary screen shot of an outbreak report system which may be incorporated into a healthcare system. As can be seen, the report shows a user the distance he or she has been from the known outbreak location(s). Furthermore, in one embodiment, the user can be provided an opportunity to check a route or address, to see if there is a current outbreak there. In one embodiment, the user can also select to view a map. Additional data may be provided about the outbreak, including risk level, vaccination availability, etc.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. A method comprising:
receiving user location data and storing the user location data;
identifying an outbreak;
backtracking contacts to the outbreak correlating historical locations of the outbreak with the stored user location data indicating past locations of the user; and
alerting the user of a potential point of contact with the outbreak when the stored user location data of the past locations of the user indicates that the user's past location had overlapped with the historical locations of the outbreak.

2. The method of claim 1, further comprising:
pruning the user location data periodically.

3. The method of claim 2, wherein pruning comprises one or more of the following: removing locations having a low risk, removing time ranges, removing locations where the user was for a short time, and removing data completely from a particular date.

4. The method of claim 1, further comprising:
receiving outbreak data identifying the outbreak from a user patient;
determining an infection period for the outbreak;
retrieving the user location data for the user patient during the infection period; and
utilizing the user location data during the infection period to identify the historical locations of the outbreak; and
utilizing the historical locations of the outbreak to identify proximity-based alerts to be sent to other users.

5. The method of claim 4, further comprising:
receiving a confirmation of infection from an alerted user; and
performing the tracing and alerting for the confirmed ill user.

6. The method of claim 4, further comprising:
maintaining user privacy while performing these processes.

7. The method of claim 4, further comprising:
generating a map of a spread of the outbreak based on the outbreak data and the identified user patients.

8. An outbreak notification system comprising:
a location receiving logic to receive location data from a user;
a user data store to store the location data; and outbreak notification receiving logic to receive notification of an outbreak, the notification including historical locations of the outbreak;

a contact trace logic to backtrack the stored location data indicating past locations of the user to determine if the user has had past contact with the outbreak based on an overlap of one of the past locations of the user and one of the historical locations of the outbreak.

9. The outbreak notification system of claim 8, further comprising:

a location correlation logic to process the location data and generate map locations.

10. The outbreak notification system of claim 8, further comprising:

a user norm calculation to calculate a normal sequence of locations for a user; and the user data store to store a user norm identification and deviations from the identified user norm, when the sequence of locations matches the normal sequence of locations for the user.

11. The outbreak notification system of claim 8, further comprising:

a pruning logic to prune data in the user data store, the pruning to reduce a volume of data.

12. The outbreak notification system of claim 11, wherein the pruning comprises one or more of: removing locations having a low risk, removing time ranges, removing locations where the user was for a short time, and removing data completely from a particular date.

13. The outbreak notification system of claim 8, further comprising:

outbreak location processor to determine one or more locations at which the outbreak can be identified as infectious.

14. The outbreak notification system of claim 13, wherein the notification may be received from one or more of the following: a news report, a press release, a notification by a system user, a notification from a healthcare provider, a notification from the Center for Disease Control or other appropriate agency.

15. The outbreak notification system of claim 13, wherein when the notification is received from a user, a patient trace logic to trace the patient's locations while the patient was infectious; and the contact trace logic to use the patient's locations.

16. The outbreak notification system of claim 8, further comprising:

an alert logic to alert a user when the user is identified as having intersected the outbreak.

17. The outbreak notification system of claim 8, further comprising:

an alert logic to alert appropriate authorities of the outbreak spread.

18. The outbreak notification system of claim 8, wherein the alert logic maintains the users' privacy in notifying the appropriate authorities.

19. The outbreak notification system of claim 8, further comprising:

a mapping logic to map a spread of the outbreak.

20. An outbreak notification system comprising:

a user data store to store location data for a plurality of users over time;

outbreak notification receiving logic to receive notification of an outbreak, the notification including a location and time; and a contact trace logic to backtrack data indicating past locations over time of a user from the user data store to determine past exposure of the user to the outbreak based on an overlap of the location and the time of the user and the outbreak.

\* \* \* \* \*